United States Patent
Etheridge et al.

(10) Patent No.: US 8,906,828 B2
(45) Date of Patent: *Dec. 9, 2014

(54) COMPOSITIONS AND METHODS FOR POST EMERGENT WEED CONTROL WITH CLETHODIM AND GIBBERELLIC ACID

(71) Applicant: Valent U.S.A. Corporation, Walnut Creek, CA (US)

(72) Inventors: Jimmy R. Etheridge, Walnut Creek, CA (US); Kevin McDonald Perry, Walnut Creek, CA (US)

(73) Assignee: Valent U.S.A., Corporation, Walnut Creek, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,603

(22) Filed: Nov. 1, 2013

(65) Prior Publication Data

US 2014/0128259 A1    May 8, 2014

Related U.S. Application Data

(60) Provisional application No. 61/722,458, filed on Nov. 5, 2012.

(51) Int. Cl.
- *A01N 43/02* (2006.01)
- *A01N 35/10* (2006.01)
- *A01N 43/12* (2006.01)
- *A01N 45/00* (2006.01)
- *A01N 57/20* (2006.01)

(52) U.S. Cl.
CPC ............... *A01N 35/10* (2013.01); *A01N 43/12* (2013.01); *A01N 45/00* (2013.01); *A01N 57/20* (2013.01)
USPC ........................................................ 504/140

(58) Field of Classification Search
None
See application file for complete search history.

(56) References Cited

U.S. PATENT DOCUMENTS 8,614,166 B2    12/2013    Hacker et al.

FOREIGN PATENT DOCUMENTS

EP    1 104 244    10/2011

OTHER PUBLICATIONS

Dickson et al., "Effect of water stress, nitrogen, and gibberellic acid on fluazifop and glyphosate activity on oats (*Avena sativa*)", Weed Science 1990, pp. 54-61.
"Supplemental Label, Plant Growth Regulator ProGibb 40%", Valent USA Corporation, Feb. 2010.
"Plant Growth Regulator, RyzUp, Solution", Valent USA Corporation, 2005.
Terry et al., "Effect of plant nitrogen concentration on the response of glyphosate-resistant corn hybrids and their progeny to clethodim and glufosinate", Weed Science 60.1 Jan.-Mar. 2010, pp. 121-125.

*Primary Examiner* — Alton Pryor
(74) *Attorney, Agent, or Firm* — Wood, Philips, Katz, Clark & Mortimer

(57) ABSTRACT

The invention relates to compositions and methods for controlling Johnsongrass or volunteer corn by application of clethodim and gibberellic acid to an area in need of weed control.

20 Claims, No Drawings

COMPOSITIONS AND METHODS FOR POST EMERGENT WEED CONTROL WITH CLETHODIM AND GIBBERELLIC ACID

FIELD OF THE INVENTION

The present invention is directed to compositions and methods for protecting crop plants from post emergent weeds with a combination of clethodim and gibberellic acid.

BACKGROUND OF THE INVENTION

The present methods are directed to applying effective amounts of clethodim and gibberellic acid to an area in need of improved weed control.

One of the major concerns of crop plant growers is the presence of undesired plants, such as weeds, in the area where the crop plant is grown. Weeds contribute to decreased crop yields because the crop plants must compete with weeds for the limited available resources such as sunlight, soil nutrients, and water. Weeds can also host pests that can increase disease rates in crop plants.

Post emergent weeds are an especially concerning issue for crop plant growers because the herbicide applied for weed control can damage the young crop plants. Growers have struggled to find methods of providing adequate post emergent weed control. One way of controlling weeds has been to apply clethodim as a foliar spray following weed emergence. Previously there was no way to increase the speed of clethodim's activity on grasses.

Johnsongrass, *Sorghum halepense*, is a grass that is considered a weed in crop plant growing areas. Johnsongrass is problematic because it grows and spreads rapidly in the crop plant growing area. Johnsongrass has also been known to develop resistance to the common herbicide glyphosate posing a serious control problem for crop plant growers. Volunteer glyphosate tolerant corn is another serious pest in crops.

Clethodim (2-[1-[[[(2E)-3-chloro-2-propen-1-yl]oxy] imino]propyl]-5-[2-(ethylthio)propyl]-3-hydroxy-2-cyclohexen-1-one) is a cyclohexanedione herbicide and a lipid (fatty acid) inhibitor. Clethodim is an effective post-emergence herbicide that is effective against perennial and annual grasses, however, symptoms of injury are typically slow to develop and are often not present for 7 to 10 days following treatment.

Clethodim typically requires 14 to 21 days to kill Johnsongrass and corn. This kill delay allows for the grass to continue to steal resources from the crop plants for up to three weeks. In addition, after each treatment growers are unsure if another treatment is necessary for several weeks which could cause over or under treatment of the crop plant environment. Therefore there is a need in the art for a more effective method of Johnsongrass and corn control.

Another issue is that when clethodim is tank mixed with herbicides to control broadleaf plants, the herbicides may antagonize the activity of clethodim on grassy weeds. It is commonly known that certain classes of broadleaf herbicides can reduce the activity of post emergence grass herbicides such as clethodim.

As explained above, there is a need in the art for a highly effective and safe post emergence weed control method, especially for the treatment of Johnsongrass.

SUMMARY OF THE INVENTION

Applicants have discovered that a combination of clethodim and gibberellic acid provides excellent post emergent weed control.

In one aspect, the invention is directed to compositions and methods for post emergent weed control comprising applying an effective amount of clethodim and an effective amount of gibberellic acid to an area in need of weed control.

In another aspect, the area in need of weed control is an area used for crop plant growth. Applicants' methods can be applied to areas growing a variety of crop plants and is effective on many types of hard-to-kill weeds.

In a further aspect, Applicants' compositions and methods are effective with a single treatment of crop plants.

DETAILED DESCRIPTION OF THE INVENTION

The present invention is directed to compositions and methods for applying clethodim and gibberellic acid to an area in need of post emergent weed control.

Gibberellic acid ("$GA_3$") is a plant hormone that promotes growth and elongation of cells. $GA_3$ has no known herbicidal activity.

Unexpectedly, Applicants found that when $GA_3$ was combined with clethodim, $GA_3$ increased the activity of clethodim. This was unexpected because $GA_3$ doesn't exhibit any herbicidal activity on its own. Because $GA_3$ is a plant growth regulator that typically improves plant growth, one skilled in the art would predict that $GA_3$ would counteract the effects of the clethodim and make clethodim a less effective herbicide. In contrast, Applicants found that $GA_3$ allowed for a more efficient kill of Johnsongrass.

In one embodiment, Applicants' invention is directed to compositions and methods for controlling weeds after they have emerged which includes applying an effective amount of clethodim and an effective amount of gibberellic acid to an area in need of weed control.

In another embodiment, the ratio of clethodim to gibberellic acid is from about 0.36:1 to about 12:1. More preferably, the ratio is from about 1.4:1 to about 5.6:1, and the most preferred ratio is about 3:1.

In a further embodiment, the effective amount of clethodim is from about 9.0 gm to about 283 gm per hectare. More preferably, the effective amount is from about 35 gm to about 141 gm per hectare, and the most preferred effective amount is about 80 gm per hectare.

In yet another embodiment, the effective amount of $GA_3$ is from about 1.25 gm to about 100 gm per hectare. More preferably, the effective amount is from about 12.5 gm to about 50 gm per hectare, and most preferred, the effective amount is about 25 gm per hectare.

Applicants' mixtures can also be applied with an effective amount of a glyphosate herbicide.

Applicants' mixtures can be applied by any convenient means. Those skilled in the art are familiar with the modes of application that include foliar applications such as spraying, dusting, and granular applications.

In one embodiment, the clethodim and $GA_3$ can be applied together as a tank mix and applied simultaneously to an area in need of weed control. Alternatively, the clethodim and $GA_3$ can be applied sequentially with either being applied first.

Applicants' compositions and methods effectively kill weeds in an area planted with crop plants. Applicants' combination of clethodim and $GA_3$ can be applied after the weeds and crop plants have germinated and emerged from the ground. The combination can be applied when the crop plants and weeds are several inches tall. For example, the weeds could be between 0.5 and 24 inches tall, or more preferably between 2 and 12 inches tall. The most preferred height of the weeds is between 2 and 6 inches tall.

Previously, growers had to wait several weeks to see results from Johnsongrass and corn herbicide treatments. Applicants' methods provide for a much quicker elimination of Johnsongrass.

In yet another embodiment, Applicants' compositions and methods can be applied successfully to crop plants and weeds that are resistant to glyphosate.

In another embodiment, the invention is directed to a method for controlling a volunteer crop. For example, in one embodiment the invention is directed to controlling volunteer corn in an area where corn growth is undesirable. An example of undesirable volunteer corn growth would be in a field where soybeans are growing.

If volunteer corn is desired to be controlled, an effective amount of a glyphosate herbicide can be added to mixtures of the present invention. In a further embodiment, the volunteer corn is resistant to glyphosate.

The herbicide combination of the present invention may be formulated to contain adjuvants, such as solvents, anti-caking agents, stabilizers, defoamers, slip agents, humectants, dispersants, wetting agents, thickening agents, emulsifiers, and preservatives which increase the long lasting activity of the actives. Other components that enhance the biological activity of these ingredients may optionally be included.

Mixtures of the present invention can be formulated to contain a liquid solvent. Examples of solvents include water and oil concentrates. Alternatively, the mixture can be formulated as a water dispersible granular composition or granular application.

Applicants' mixtures can also include one or more herbicides. An example of this is adding an auxin, such as dicamba, or a glyphosate herbicide. Further, the mixtures can include additional ingredients to increase the effectiveness of the active ingredients.

The mixture of the present invention can be applied to any environment in need of weed control. The environment in need of weed control may include any area that is desired to have a reduced number of weeds or to be free of weeds. For example, the herbicide combination can be applied to an area used to grow crop plants, such as a field, orchard, or vineyard. For example, Applicants' compositions and methods can be applied to areas where soybeans, corn, peanuts, and cotton are growing. In a preferred embodiment, the mixture is applied in an area where a broadleaf crop (soybean, cotton, peanut, orchard, vineyard, forages) is growing. The weed may be a volunteer crop carried over from the previous planting season, for example, corn would be a volunteer crop/weed in a soybean field. The crop may be GMO or non-GMO. The weed may be GMO or non-GMO. The term "GMO crops" as used herein refers to crops grown from genetically modified organisms.

Mixtures of the present invention would preferably be as easy as possible for the end user to apply. For example, in some cases it would be desirable to apply $GA_3$ and clethodim in the same mix. $GA_3$ is incompatible with a premix of clethodim and clethodim may require the use of a NIS for optimal herbicide performance. Accordingly, it has been discovered that a non-ionic surfactant ("NIS") could be added to $GA_3$. Adding a NIS to $GA_3$ would reduce the number of products that the end user has to add to the mix. In previous tank mixes, the end user would have to add clethodim, $GA_3$ and a NIS to the mixer. However, in this embodiment, the end user would only have to add two components, the $GA_3$ with a NIS and clethodim. This embodiment would also reduce end user errors because fewer components must be measured.

The disclosed embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The term "effective amount" means the amount of the formulation that will kill a weed. The "effective amount" will vary depending on the formulation concentration, the type of plants(s) being treated, the severity of the weed infestation, the result desired, and the life stage of the weeds during treatment, among other factors. Thus, it is not always possible to specify an exact "effective amount." However, an appropriate "effective amount" in any individual case may be determined by one of ordinary skill in the art.

The following examples are intended to illustrate the present invention and to teach one of ordinary skill in the art how to use the formulations of the invention. They are not intended to be limiting in any way.

EXAMPLES

SelectMax® Herbicide (available from Valent U.S.A. Corporation) contains 12.6% clethodim and was used throughout the examples as the source of clethodim. ProGibb® 4% (available from Valent BioSciences Corporation) contains 4% $GA_3$ and was used in Examples 1-4 as the source of $GA_3$. A 40% $GA_3$ formulation was used in Examples 5 and 6.

Example 1

In order to determine the efficacy of combinations of clethodim and $GA_3$, numerous treatments were applied to plots in an area with abundant Johnsongrass growth.

The percent control of Johnsongrass plants was evaluated at 7, 18 and 28 days following the treatment. The results of this study can be found below in "Table 1. Effect of Clethodim and $GA_3$ Treatments on Johnsongrass (% control)."

TABLE 1

Effect of Clethodim and $GA_3$ Treatments on Johnsongrass (% control)

| Treatment | Rate | 7 DAT | 18 DAT | 28 DAT |
|---|---|---|---|---|
| Untreated Control | NA | 3.33 | 0 | 0 |
| $GA_3$ | 5 g ai/a (5 fl oz/a of ProGibb 4%) | 0 | 0.32 | 0 |
| $GA_3$ | 25 g ai/a (25 fl oz/a of ProGibb 4%) | 0 | 0 | 0 |
| Clethodim* | 32 x g ai/a (9 fl oz/a of Selectmax) | 37.21 | 85.66 | 89.26 |
| $GA_3$ + Clethodim* | 5 g ai/a (5 fl oz) 32 × g ai/a | 77.99 | 96.94 | 88.68 |
| $GA_3$ + Clethodim* | 25 g ai/a (25 fl oz) 32 × g ai/a | 77.01 | 94.92 | 89.60 |

*Treatment included 0.25% v/v of a non-ionic surfactant and 2.5 lb/acre of ammonium sulfate (AMS).

The percent control refers to the amount of dead tissue on the plants present. It would be dead plants plus desiccated foliage on partially killed plants.

Applicants unexpectedly found that combinations of clethodim and $GA_3$ resulted in superior Johnsongrass control. For example, Applicants found that seven days following treatment clethodim controlled Johnsongrass at 37.21%. Remarkably, the clethodim and $GA_3$ treatments controlled Johnsongrass at over 77%. This indicates that $GA_3$ more than doubles the activity of clethodim on Johnsongrass. Decreasing the time until the weeds' death will allow for a higher crop yield as the weeds are being eliminated faster and are no longer competing with the crop plants for resources.

Example 2

A further study was performed in order to confirm the effect clethodim and $GA_3$ treatments have on corn. Glyphosate resistant corn was planted with a conventional four-row planter. Treatments were applied 28 days after the plantings.

The percent corn control was evaluated at 6, 9 and 29 days following the treatments. The results of this study can be found below in "Table 2. Effect of Clethodim and $GA_3$ Treatments on corn (% control).

This study confirmed that the activity of clethodim is significantly increased by the presence of $GA_3$.

TABLE 2

Effect of Clethodim and $GA_3$ Treatments on Corn (% control)

| Treatment | Rate | 6 DAT | 13 DAT | 29 DAT |
|---|---|---|---|---|
| Untreated Control | NA | 0 | 0 | 0 |
| $GA_3$* | 3 g ai/a | 0 | 0 | 0 |
| $GA_3$* | 10 g ai/a | 0 | 0 | 0 |
| Clethodim* | 32 gm ai/a | 48.33 | 88.33 | 96.00 |
| $GA_3$ + Clethodim* | 0.5 g ai/a 32 gm ai/a | 46.67 | 86.67 | 95.67 |
| $GA_3$ + Clethodim* | 1 g ai/a 32 gm ai/a | 50.00 | 86.67 | 93.33 |
| $GA_3$ + Clethodim* | 3 g ai/a 32 gm ai/a | 66.67 | 93.33 | 98.00 |
| $GA_3$ + Clethodim* | 10 g ai/a gm ai/a | 66.67 | 91.67 | 96.00 |

*Treatment included 0.25% v/v of a non-ionic surfactant and 2.5 lb/acre of ammonium sulfate.

Volunteer glyphosate tolerant-corn is a weed in soybeans and sometimes must be killed prior to planting corn. Clethodim is used to control the volunteer corn. This study confirmed that the activity of clethodim on corn is significantly increased in the presence of $GA_3$.

Example 3

A further study was done in Falmouth, Ind. Volunteer glyphosate tolerant corn was sprayed with clethodim and $GA_3$. The percent corn control was recorded at 8 and 18 days after treatment. The results of the study are shown in "Table 3. Effect of Clethodim and $GA_3$ Treatments on Corn."

TABLE 3

Effect of Clethodim and $GA_3$ Treatments on Corn

| | | 8 DAT | | 18 DAT | |
|---|---|---|---|---|---|
| | | Single plant | Clump | Single plant | Clump |
| | | % Volunteer corn control | | | |
| 1 | SelectMax ® 9 fl oz/A | 50 | 30 | 90 | 60 |
| 2 | SelectMax ® 9 fl oz/A + RUSG ($GA_3$) 1 g ai/A | 60 | 40 | 98 | 80 |
| 3 | SelectMax ® 9 fl oz/A + RUSG ($GA_3$) 10 g ai/A | 75 | 50 | 100 | 90 |
| 4 | Untreated | 0 | 0 | 0 | 0 |

Example 4

A further study was done in Urbana, Ill. Volunteer glyphosate tolerant corn was sprayed with clethodim and $GA_3$. The percent corn control was recorded at 8 days after treatment. The results of the study are shown in "Table 4. Effect of Clethodim and $GA_3$ on Corn."

TABLE 4

Effect of Clethodim and $GA_3$ on Corn

| | % Control 8 DAT |
|---|---|
| SelectMax ® | 35 |
| SelectMax ® + ProGibb ® 1 g ai/A | 55 |
| SelectMax ® + ProGibb ® 10 g ai/A | 85 |

Example 5

A further study was done in Greenville, Miss. Volunteer corn was sprayed with clethodim, $GA_3$, and the glyphosate herbicide Roundup PowerMAX® (available from Monsanto). Volunteer corn is corn that survives as grain in the field and germinates in the field the following season. Volunteer corn is considered a weed. The percent of corn control was recorded at 14 and 26 days after treatment. This study was designed to determine if a 40% $GA_3$ formulation would act as a spray adjuvant and perform equal to or superior to the commercial ammonium sulfate ("AMS") product when SelectMax® is applied post emergence for the control of Roundup Ready ("RR") volunteer corn. The results of this study are shown below in Table 5.

TABLE 5

| | Product | Formulation | Dose Rate | % Control of RR Volunteer Corn | |
|---|---|---|---|---|---|
| | | | | 14 DAT | 26 DAT |
| Treatment 1 | SelectMax ® (clethodim) | 1 LBAI/GAL | 9 FLOZ/A | 45 | 72.7 |
| | Roundup PowerMAX ® (glyphosate) | 4.5 LBAI/GAL | 22 FLOZ/A | | |
| | AMS | 100% | 2.5 LB/A | | |

TABLE 5-continued

| | Product | Formulation | Dose Rate | % Control of RR Volunteer Corn | |
|---|---|---|---|---|---|
| | | | | 14 DAT | 26 DAT |
| Treatment 2 | SelectMax ® (clethodim) | 1 LBAI/GAL | 9 FLOZ/A | 61.7 | 87.3 |
| | Roundup PowerMAX ® (glyphosate) | 4.5 LBAI/GAL | 22 FLOZ/A | | |
| | AMS | 100% | 2.5 LB/A | | |
| | GA$_3$ formulation | 40% | 6 GMAI/A | | |

Volunteer corn control was significantly superior at both 14 and 26 days after post emergence in Treatment 2 (containing GA$_3$ 40% formulation) compared to Treatment 1.

Example 6

A further study was done in Greenville, Miss. Volunteer corn was sprayed with clethodim and GA$_3$. The percent corn control was recorded at 21 days after treatment. This study was designed to determine if a 40% GA$_3$ formulation would act as a spray adjuvant and perform equal to or superior to the commercial ammonium sulfate ("AMS") product when SelectMax is applied post emergence for the control of Roundup Ready ("RR") volunteer corn. The results of this study are shown below in Table 6.

TABLE 6

| | Product | Formulation | Dose Rate | % Control of RR Volunteer Corn 21 DAT |
|---|---|---|---|---|
| Untreated control | n/a | n/a | n/a | 0 |
| Treatment 1 | SelectMax ® (clethodim) | 1 LBAI/GAL | 6 FLOZ/A | 82 |
| | Clarity ® (dicamba) | 4.0 LBAI/GAL | 1 PT/A | |
| | Roundup PowerMAX ® (glyphosate) | 4.5 LBAI/GAL | 22 FLOZ/A | |
| | AMS | 100% | 2.5 LB/A | |
| Treatment 2 | SelectMax ® (clethodim) | 1 LBAI/GAL | 6 FLOZ/A | 96 |
| | Clarity ® (dicamba) | 4.0 LBAI/GAL | 1 PT/A | |
| | Roundup PowerMAX ® (glyphosate) | 4.5 LBAI/GAL | 22 FLOZ/A | |
| | GA$_3$ formulation | 40% | 3 GMAI/A | |

Volunteer corn control was significantly superior at 21 days after post emergence application of SelectMax® in combination with GA$_3$ compared to SelectMax® applied with the commercial standard ammonium sulfate or compared to the untreated control. Clarity® is a commercially available auxin, specifically dicamba (diglycolamine) (available from BASF).

The invention claimed is:

1. An agricultural composition comprising an effective amount of clethodim and an effective amount of gibberellic acid (GA$_3$), wherein the clethodim and GA$_3$ applied to ether provides improved weed control over clethodim or GA$_3$ applied alone.

2. The composition of claim 1 wherein the clethodim and GA$_3$ are in a ratio range of from about 0.36:1 to about 12:1.

3. The composition of claim 2 wherein the clethodim and GA$_3$ is are in a ratio of about 3:1.

4. The composition of claim 1 further comprising an effective amount of a glyphosate herbicide.

5. A method for killing Johnsongrass in an area planted with crop plants or an area without crop plants, comprising applying an effective amount of the composition of claim 1 as a pre-emergence or post emergence application wherein the clethodim and GA$_3$ applied together provides improved Johnsongrass control over clethodim or GA$_3$ applied alone.

6. The method of claim 5 wherein the clethodim and GA$_3$ are applied when the Johnsongrass is about 2 to about 12 inches tall, or before the Johnsongrass germinates.

7. The method of claim 5 wherein the clethodim and GA$_3$ are applied when the crop plants are about 1 to about 36 inches tall.

8. The method of claim 5 wherein the crop plants are a broadleaf crop.

9. The method of claim 5 wherein the Johnsongrass or crop plants are resistant to glyphosate.

10. A method for Johnsongrass control comprising applying an effective amount of clethodim and an effective amount of gibberellic acid (GA$_3$) to an area in need of Johnsongrass control, wherein the clethodim and GA$_3$ applied to ether provides improved Johnsongrass control over clethodim or GA$_3$ applied alone.

11. The method of claim 10 wherein the clethodim and GA$_3$ are in a ratio range of from about 0.36:1 to about 12:1.

12. The method of claim 11 wherein the clethodim and GA$_3$ are in a ratio of about 3:1.

13. The method of claim 10 wherein the effective amount of the clethodim is applied at a rate of from about 0.01 to about 0.25 lb ai/a.

14. The method of claim 10 wherein the effective amount of the GA$_3$ is applied at a rate of from about 1.25 qm to about 100 qm per hectare.

15. The method of claim 10 wherein the clethodim and GA$_3$ are applied by spraying, as a dust or granular application.

16. The method of claim 10 wherein the clethodim and GA$_3$ are applied simultaneously or sequentially.

17. The method of claim 10 wherein the effective amount of the clethodim is from about 9.0 gm to about 283 gm per hectare.

18. A method for volunteer corn control comprising applying an effective amount of clethodim and an effective amount of gibberellic acid (GA$_3$) to an area in need of volunteer corn control, wherein the clethodim and GA3 applied together provides improved volunteer corn control over clethodim or GA3 applied alone.

19. The method of claim 18 further comprising an effective amount of a glyphosate herbicide.

20. The method of claim 19 wherein the volunteer corn is resistant to glyphosate.

\* \* \* \* \*